(12) United States Patent
Kosik et al.

(10) Patent No.: US 10,864,206 B2
(45) Date of Patent: Dec. 15, 2020

(54) TREATMENT OF NEURODEGENERATIVE CONDITIONS BY DISRUPTION OF RHES

(71) Applicant: The Regents of the University of California, Oakland, CA (US)

(72) Inventors: Kenneth Kosik, Santa Barbara, CA (US); Israel Hernandez, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/162,239

(22) Filed: Oct. 16, 2018

(65) Prior Publication Data

US 2019/0083480 A1 Mar. 21, 2019

Related U.S. Application Data

(63) Continuation of application No. PCT/US2018/013712, filed on Jan. 15, 2018.

(60) Provisional application No. 62/446,628, filed on Jan. 16, 2017.

(51) Int. Cl.
| | |
|---|---|
| *A61K 31/4545* | (2006.01) |
| *A61K 31/4709* | (2006.01) |
| *A61P 25/28* | (2006.01) |
| *A61K 31/12* | (2006.01) |
| *A61P 25/00* | (2006.01) |
| *A61P 25/14* | (2006.01) |
| *A61P 25/16* | (2006.01) |
| *A61K 31/223* | (2006.01) |

(52) U.S. Cl.
CPC .......... *A61K 31/4545* (2013.01); *A61K 31/12* (2013.01); *A61K 31/223* (2013.01); *A61K 31/4709* (2013.01); *A61P 25/00* (2018.01); *A61P 25/14* (2018.01); *A61P 25/16* (2018.01); *A61P 25/28* (2018.01)

(58) Field of Classification Search
None
See application file for complete search history.

(56) References Cited

U.S. PATENT DOCUMENTS

| | | |
|---|---|---|
| 2009/0087868 A1 | 4/2009 | Wang et al. |
| 2013/0303564 A1 | 11/2013 | Pahan |

FOREIGN PATENT DOCUMENTS

| | | |
|---|---|---|
| WO | 2016-109649 A1 | 7/2016 |

OTHER PUBLICATIONS

Vargiu "The small GTP-binding protein, Rhes, regulates signal transduction from G protein-coupled receptors" oncogene 23:559-568 (Year: 2004).*

(Continued)

*Primary Examiner* — Adam Weidner

(57) ABSTRACT

The invention is directed to the treatment of tauopathic neurodegenerative conditions and the underlying processes thereof. Based on the discovery that Rhes acts as a negative regulator of normal tau clearance, the compositions and methods of the invention may be applied to inhibit Rhes and reduce pathogenic tau aggregation. Rhes may be disrupted by disrupting RAS2D gene expression or reducing the abundance of Rhes protein in neurons. Additionally, post-translational modifications of Rhes may be targeted, including the disruption of Rhes farnesylation by the administration of farnesyltransferase inhibitors.

2 Claims, 2 Drawing Sheets

(56) References Cited

OTHER PUBLICATIONS

Trabalzini "Ras Signaling" published by humana press (excerpt only) (Year: 2014).*
Chirichigno "Stress-induced mitochondrial depolarization and oxidative damage in PSP cybrids" Brain Research 951 (2002) 31-35 (Year: 2002).*
Du "Mitochondrial medicine for neurodegenerative diseases" Int J Biochem Cell Biol. May 2010 ; 42(5): 560-572 (Year: 2010).*
Albers "Frontal Lobe Dysfunction in Progressive Supranuclear Palsy: Evidence for Oxidative Stress and Mitochondrial Impairment" J. Neurochem., vol. 74, No. 2 (Year: 2000).*
Cherry "microglial neuroinflammation contributes to tau accumulation in chronic traumatic encephalopathy" acta neuropath comm 4:112 (Year: 2016).*
Faden "Chronic Neurodegeneration After Traumatic Brain Injury: Alzheimer Disease, Chronic Traumatic Encephalopathy, or Persistent Neuroinflammation?" neurothera 12:143-150 (Year: 2015).*
Mealer, R. G. et al., "Rhes, a striatal-selective protein implicated in huntington disease, binds Beclin-1 and activates autophagy", The Journal of Biological Chemistry, 2014, vol. 289, No. 6, pp. 3547-3554 See abstract; pp. 3549-3551 ; figures 3-5.
Gratuze, M. et al., "Is huntington's disease a tauopathy?", Brain, 2016, vol. 139, pp. 1014-1025 See abstract: pp. 1019-1023.
Miller, J.P. et al., "A genome-scale RNA-interference screen identities RRAS signaling as a pathologic feature of huntington's disease", PLoS One, 2012, vol. 8. Issue 11, Article No. e1003042, Internal pp. 1-22. See abstract.
Farnesyltransferase haplodeficiency reduces neuropathology and rescues cognitive function in a mouse model of Alzheimer disease. Cheng S, Cao D, Hottman DA, Yuan L, Bergo MO, Li L. J Biol Chem. Dec. 13, 2013;288(50):35952-60: Entire document.
Hernandez et al., A farnesyltransferase inhibitor activates lysosomes and reduces tau pathology in mice with tauopathy, Sci. Transl. Med. 11, eaat3005 (2019).
Lee et al., Rhes Suppression Enhances Disease Phenotypes in Huntington's Disease Mice, 2014, J Huntington's Disease 3: 65-71.
Spano et al., Rhes Is Involved in Striatal Function, Mol Cell Bio, Jul. 2004, p. 5788-5796.
Harrison and He, Rhes and AGS1/Dexras1 Affect Signaling by Dopamine D1 Receptors Through Adenylyl Cyclase, J Neurosci Res 2011, 89:874-882.
Wennerberg et al., The Ras Superfamily at a Glance, Journal of Cell Science 118, 843-846.
Newlaczyl et al., Quantification of spatiotemporal patterns of Ras isoform expression during development, Scientific Reports 7: Article 41927 (2017).

* cited by examiner

TREATMENT OF NEURODEGENERATIVE CONDITIONS BY DISRUPTION OF RHES

CROSS-REFERENCE TO RELATED APPLICATIONS

This application is a continuation application of PCT International Patent Application No. PCT/US2018/013712, entitled "Treatment of Neurodegenerative Conditions by Disruption of Rhes," filed on Jan. 15, 2018, which claims priority to U.S. Provisional Patent Application Ser. No. 62/446,628, entitled "Treatment of Neurodegenerative Conditions by Disruption of Rhes," filed on Jan. 16, 2017, each of which is incorporated by reference herein in its entirety.

STATEMENT REGARDING FEDERALLY SPONSORED RESEARCH OR DEVELOPMENT

Not applicable

BACKGROUND OF THE INVENTION

Tauopathies are a diverse group of neurodegenerative diseases characterized by the accumulation of neurofibrillary tangles, which are aggregates of tau, a microtubule-stabilizing protein. The progressive accumulation of these aggregates in the brain leads to impaired neural function and cell death. Although tau-related diseases, including Alzheimer's disease and chronic traumatic encephalopathy, are serious public health problems, no disease-modifying treatment currently exists for these conditions. Efforts to develop treatment have focused directly on the tau protein as a target for drugs, however, the approach has been largely without success.

Autophagy, a lysosomal degradation pathway, has been implicated as an important pathway implicated in neuronal health and disease. In healthy neurons, autophagy is believed to clear tau and prevent the formation of tau aggregates. Regulation of autophagy is not well understood. The GTPase Rhes has been implicated in the regulation of autophagy, with conflicting roles. Rhes has been shown to inhibit autophagy via its activation of the mTOR signaling kinase. Paradoxically, Rhes has been shown to activate autophagy via its interactions with the beclin-Bcl2 complex.

Accordingly, there remains a need in the art for an improved understanding of the mechanisms which regulate tau clearance and aggregation, and there remains a strong need for novel therapeutic agents and methods to treat, reverse, and prevent the formation of neurofibrillary tangles.

SUMMARY OF THE INVENTION

The inventors of the present disclosure have discovered that regulation of autophagy by Rhes plays a critical role in the pathogenic aggregation of tau. Specifically, farnesylation of Rhes appears to serve as a switch between its inhibitory and activating effects on autophagy. In farnesylation of Rhes, the addition of a lipidic moiety to the protein enables Rhes attachment to the plasma membrane and this form of post-translationally modified Rhes is apparently necessary for the negative action of Rhes on tau clearance. The inventors of the present disclosure have demonstrated that when farnesylation of Rhes is disrupted, tau clearance is enhanced.

The compositions and methods disclosed herein encompass agents and their administration to patients suffering from tauopathies. The scope of the invention encompasses novel methods of promoting autophagy and reducing the formation of neurofibrillary tangles in neurons by the disruption of Rhes. The invention provides compositions and methods for the inhibition of tau aggregation and for treating tauopathies. In another aspect, the use of farnesyltransferase inhibitors in the disruption of Rhes is disclosed and provides the art with a novel means of combating tauopathies utilizing previously developed and well tolerated drugs.

DETAILED DESCRIPTION OF THE INVENTION

Figure 1:
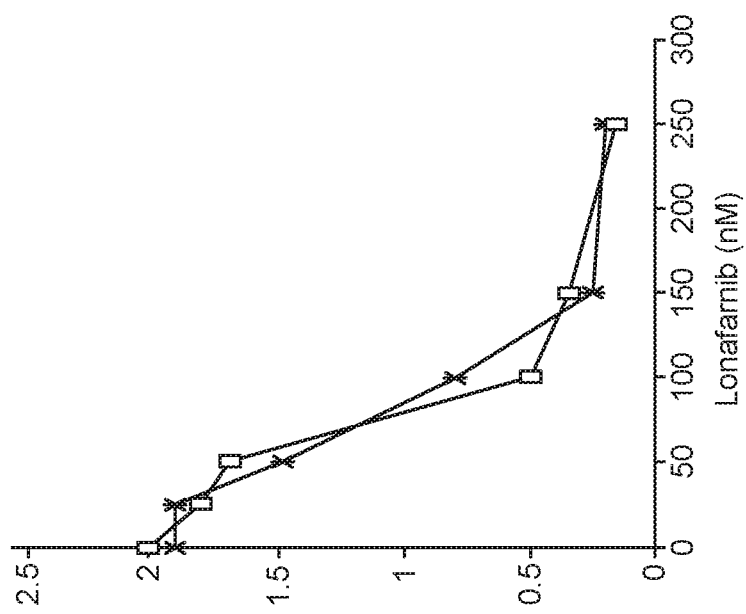
FIG. 1. Mouse cultured neurons overexpressing Rhes display an aberrant accumulation of phosphorylated tau. This accumulation is reduced in neurons treated with increasing concentrations of the farnesyl transferase inhibitor, Lonafarnib (assayed between 25 to 250 nM). The two lines represent results for separate culture replications.

Rhes Disrupting Agents.

The scope of the invention encompasses what will be referred to herein as a "Rhes-disrupting agents." The Rhes-disrupting agents of the invention include any composition of matter that inhibits, reduces, reverses, or prevents Rhes-mediated aggregation of tau in neurons or other cells. The Rhes protein (Uniprot Accession Number Q96D21) in humans is encoded by the RASD2 gene, also known as the Ras D Family Member 2 gene. Rhes is a signaling GTPase implicated in several biological processes by its activation of various downstream effectors. The Rhes-disrupting agents of the invention will include any composition of matter that reduce the expression, translation, post-translational modification, or autophagy-inhibiting activities of Rhes.

In one embodiment, the Rhes-disrupting agent comprises a composition which disrupts RASD2 gene expression, for example the agent may comprise a CRISPR/Cas9 construct, an RNAi silencing construct, a TALEN, or other nucleic acid composition, the expression of which results in suppression of RASD2 gene expression. In another embodiment, the Rhes-disrupting agent comprises a composition which neutralize or renders Rhes proteins non-functional or which reduces the abundance of Rhes in the cell. For example the agent may comprise an anti-Rhes antibody or aptamer.

The tauopathic effects of Rhes require post-translational modification of the Rhes protein. Accordingly, in one aspect, the Rhes-disrupting agent of the invention encompass any composition which disrupt normal post-translational modifications of Rhes protein. The Rhes protein is acted upon by farnesyl transferases which attach hydrophobic farnesyl groups to the protein's carboxyl terminus. Accordingly, in one embodiment, the Rhes-disrupting agents of the invention encompass farnesyltransferase inhibitors, including any agent which prevents the attachment of farnesyl groups to Rhes and thus reduces its tauopathic activity by preventing its attachment to the inner membrane.

Various farnesyltransferase inhibitors are known in the art. Some of these compounds were developed after it was discovered that overactivated Ras GTPases are implicated in various forms of cancer. While farnesyltransferase inhibitors have had mixed success in the treatment of cancer, some of the available farnesyltransferase inhibitors have excellent bioavailability, are able to cross the blood-brain barrier, have good pharmacokinetics, and exhibit low toxicity. Accordingly, many of these agents are well suited for the treatment of tauopathies due to their relatively advanced state of development and proven tolerability.

Accordingly, in one embodiment, the Rhes-disrupting agent of the invention comprises a farnesyltransferase inhibitor which inhibits the farnesylation of Rhes. The farnesyltransferase inhibitor may be any farnesyltransferase inhibitor known in the art. The farnesyltransferase inhibitor may be selected from the group consisting of: lonafarnib, tipifarnib, gingerol, gliotoxin, α-hydroxy farnesyl phosphonic acid, manumycin A, chaetomellic acid A, clavaric acid, FPT Inhibitor I, FPT Inhibitor II, FPT Inhibitor III, FTase Inhibitor I, FTase Inhibitor II, FTI-276 trifluoroacetate salt, GGTI-297, FTI-277 trifluoroacetate salt, and L-744,832 dihydrochloride.

Additional farnesyltransferase inhibitors that may be used in the practice of the invention include compositions described in: U.S. Pat. No. 8,828,356, entitled "Farnesyltransferase inhibitors for treatment of laminopathies, cellular aging and atherosclerosis," by Gordon et al.; U.S. Pat. No. 5,925,641, entitled "Farnesyltransferase inhibitor," by Kanda et al.; PCT International Patent Application Publication Number WO/2002074747, entitled "Farnesyltransferase inhibitors," by Claiborne et al.; and U.S. Pat. No. 7,101,897, entitled "Farnesyl transferase inhibitors," by Wardleworth et al.

Pharmaceutical Compositions.

The scope of the invention encompasses various pharmaceutical compositions and methods of using such pharmaceutical compositions. The pharmaceutical compositions of the invention will comprise one or more Rhes-disrupting agents; i.e. the composition may comprise a single Rhes-disrupting agent or may comprise a combination of two or more such agents.

The pharmaceutical compositions of the invention may comprise constituents in addition to the one or more Rhes-disrupting agents. For example, the pharmaceutical composition may comprise one or more additional pharmaceutically active agents. The pharmaceutical composition may comprise additional compositions such as pharmaceutically acceptable carriers, excipients, diluents, buffers, salts, or release-modulating agents In one embodiment, the invention comprises a pharmaceutical composition for the treatment of a tauopathy wherein the pharmaceutical composition comprises one or more Rhes-disrupting agents.

In one embodiment, the invention comprises a pharmaceutical composition for the reducing the abundance of Rhes protein in neurons, wherein the pharmaceutical composition comprises one or more Rhes-disrupting agents.

In one embodiment, the invention comprises a pharmaceutical composition for promoting autophagy of tau in neurons wherein the pharmaceutical composition comprises one or more Rhes-disrupting agents.

In one embodiment, the invention comprises a pharmaceutical composition for inhibiting Rhes attachment to the cell membrane, wherein the pharmaceutical composition comprises one or more Rhes-disrupting agents.

METHODS OF THE INVENTION

The scope of the invention encompasses novel methods directed to the treatment of various neurodegenerative conditions comprising tauopathies. In one implementation, the scope of the invention encompasses a method of treating a tauopathy in a subject in need of treatment by the administration of a pharmaceutically effective amount of a pharmaceutical composition comprising a Rhes-disrupting agent.

The tauopathy may comprise any neurodegenerative condition wherein abnormal tau accumulation is present. The tauopathy may be any condition encompassing the aberrant processing of tau, the pathologic aggregation of tau proteins, or neurodegeneration resulting from dysregulated, dysfunctional, or mutant tau. Exemplary tauopathies include a condition selected from the group consisting of: Pick's disease, progressive supranuclear palsy, corticobasal degeneration, argyrophilic grain disease, Alzheimer's disease, chronic traumatic encephalopathy (e.g. associated with head trauma), Niemann-Pick-C, Guam-ALS-Parkinson's-dementia, post-encephalitic Parkinson's disease, and Subacute sclerosing panencephalitis.

The subject of the administration may be a human, for example a human patient afflicted with or at risk for a tauopathy. Alternatively, the subject of the administration may be an animal, of any species, for example, a veterinary subject, or a test animal. In the case of a non-human animal, it will be understood that the invention is directed to the appropriate Rhes orthologs and/or homologs in that species. The scope of the invention also extends to the administration of the pharmaceutical compositions of the invention to cells, cell cultures, and explanted tissues.

The pharmaceutical composition may be administered as a treatment. The treatment may be a therapeutic treatment applied to a subject suffering from a tauopathy, the treatment being administered, for example, to ameliorate pathogenic tau aggregation, to reverse pathogenic tau aggregation, to prevent pathogenic tau aggregation, to improve neurological and/or cognitive function. In some embodiments, the treatment is a preventative treatment administered to a subject at risk of a tauopathy, wherein such administration prevents or delays the onset of the disease phenotype. Risk factors may include age, e.g. age over 40, over 45, over 50, over 55, over 65 years, or genetic predisposition (e.g. carriers of the apolipoprotein E ε4 allele or Tau mutations). In some embodiments, the administration of the pharmaceutical composition will be referred to as decreasing, reducing, or otherwise changing the magnitude of tau aggregation, neurodegenerative symptoms, or related process. Such decreases may be defined with respect to the magnitude of tau aggregation, neurodegenerative symptoms, or related processes observed in untreated controls or in subjects prior to treatment. Likewise, treatment may be described as increasing tau clearance, or as improving neurological and/or cognitive function in treated subjects. Such increases or improvements may be defined with respect to the magnitude of tau clearance, neurological and/or cognitive function or related measures observed in untreated controls or in subjects prior to treatment.

The pharmaceutical composition may be administered by any appropriate means. For example, administration may be oral, intravenous, intracorporeal, or topical. The pharmaceutical compositions of the invention may be formulated for the desired mode of administration.

The pharmaceutical composition can be administered at any effective dosage, i.e. a dosage having a physiological effect with regards to Rhes-mediated tau aggregation. Exemplary dosages may be dosages which result in physiological concentrations of Rhes-disrupting agent in the range of 1 nM to 1 mM, for example in the range of 5 nM to 500 nM. Exemplary daily dosages are in the range of 1 ng per kilogram body weight to 500 mg per kilogram body weight. Different compounds will have different ideal dosages, as may be determined by one of skill in the art. For example, Lonafarnib, has been demonstrated to be effective and well tolerated at a dose of 100-150 mg/m2 body surface area.

In a related implementation, the scope of the invention encompasses a method of reducing the abundance of Rhes in neurons of a subject by the administration of a pharmaceutically effective amount of a pharmaceutical composition comprising a Rhes-disrupting agent. Such method may be applied to inhibit expression of RASd2 or to directly neutralize Rhes proteins.

In a related implementation, the scope of the invention encompasses a method of promoting autophagy of tau in neurons of a subject by the administration of a pharmaceutically effective amount of a pharmaceutical composition comprising a Rhes-disrupting agent. Such method may be applied to inhibit, reduce, reverse or prevent tau aggregation in neurons or other cells of the subject.

In another related implementation, the scope of the invention encompasses a method of disrupting Rhes binding to the membrane in neurons of a subject by the administration of a pharmaceutically effective amount of a pharmaceutical composition comprising a Rhes-disrupting agent.

In another related implementation, the scope of the invention encompasses a method of inhibiting the farnesylation of Rhes in a subject by the administration of a pharmaceutically effective amount of a pharmaceutical composition comprising a Rhes-disrupting agent, wherein the Rhes-disrupting agent comprises a farnesyltransferase inhibitor.

In another aspect, the scope of the invention encompasses a method of using a Rhes-disrupting agent for the manufacture of a medicament for use in the treatment of a tauopathy.

EXAMPLES

Example 1. Farnesylation Inhibition Attenuates Tau Pathology in rTg4510 Mice

Lonafarnib is a potent farnesyl transferase inhibitor with a Ki in the nM range, that crosses the blood brain barrier and has few side effects in humans.
Mouse cultured neurons overexpressing Rhes display an aberrant accumulation of phosphorylated tau. This accumulation is reduced in neurons treated with increasing concentrations of the farnesyl transferase inhibitor, Lonafarnib (assayed between 25 to 250 nM) (FIG. 1).

Based on these results, the effects of lonafarnib administration were further tested in the rTg4510 mouse, a widely used model for frontotemporal dementia. These mice develop tau tangles in the cerebral cortex by 4 months of age and in the hippocampus by 5.5 months. By 5.5 months, the mice also lose about 60% of their hippocampal CA1 neurons. Spatial memory deficits become apparent by 2.5 to 4 months of age; however electrophysiological properties of cortical neurons are detected before the accumulation of tau pathology. To determine precisely the effects of lonafarnib, the time course for the onset of pathology in rTg4510 was replicated. MC1 immunoreactivity, corresponding to neurofibrillary tangles throughout hippocampus, amygdala, entorhinal cortex and cerebrocortex, was first detected at ~16 weeks and progressed by 20 weeks to a mean of $92.99 \pm 13.626$ $MC1^+$ cells/mm$^2$ in the cerebral cortex, and $67.57 \pm 13.113$ cells/mm$^2$ in the hippocampus. WT mice showed no detectable $MC1^+$ neurons.

Lonafarnib treatment was initiated when the animals were ten weeks old. The drug was resuspended in 20% HBCD and gavage fed, five days on and five days off at 80 mg/Kg/day. The drug was remarkably effective in reducing MC1 immunoreactivity. When evaluated at 20-weeks, the cortex ($44.27 \pm 4.064$ MC1+ cells/mm$^2$) and hippocampus ($13.38 \pm 2.615$ MC1+ cells/mm$^2$) compared to either vehicle-treated ($84.15 \pm 5.050$ cells/mm$^2$ in cortex and $42.01 \pm 3.305$ cells/mm$^2$ in hippocampus; cortex $p=7.2 \times 10^{-3}$, hippocampus $p=6.4 \times 10^{-3}$), or untreated (cortex $p=3.5 \times 10^{-3}$, hippocampus $p=2.4 \times 10^{-5}$) age-matched transgenic mice, MC1 immunoreactivity was significantly reduced. In contrast to chronic administration, lonafarnib was ineffective as an acute intervention when gavage-treated daily for 2 weeks (80 mg/Kg/day) in 20 week-old rTg4510 mice, after tau pathology was fulminant.

Chronic lonafarnib treatment also prevented the reduction in brain size among aged transgenic mice. Coronal section area of littermate controls and transgenic mice did not differ at five weeks, but significantly diminished by 20 weeks, as mice aged. Lonafarnib-treated transgenic mice at 20-weeks had significantly larger coronal brain areas than both vehicle and Untreated age-matched transgenic mice.

Microglia counts, assessed by Iba1 at 5 and 20 weeks, were significantly decreased with age in control littermates in cortex (p=0.049) and hippocampus (p=0.014), but remained elevated in 20 week transgenic mice. At five weeks, no statistical difference was observed in microglial counts between control and transgenic mice; however, by 20 weeks, this difference was significant in both cortex and hippocampus. Lonafarnib significantly reduced hippocampal microgliosis in 20-week old transgenic mice compared to age matched untreated transgenic mice.

Figure 2:
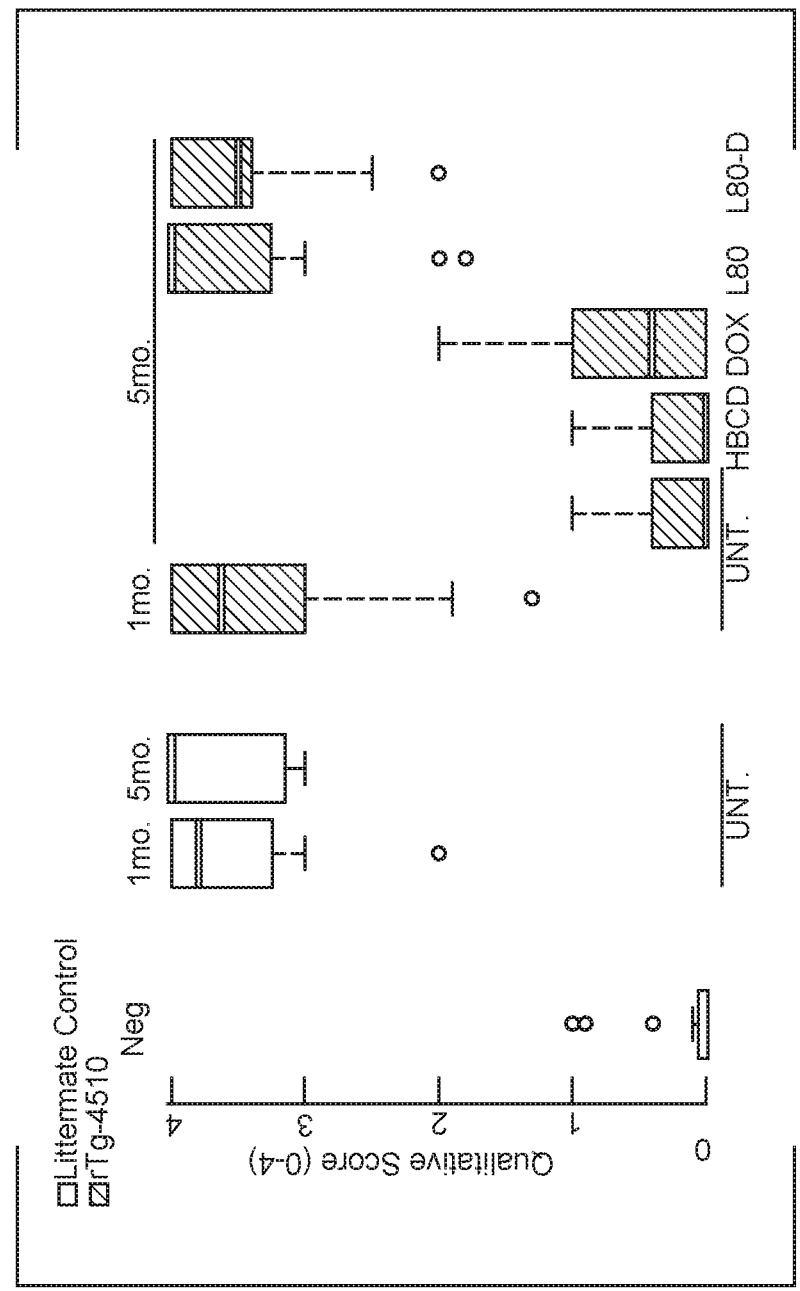
FIG. 2 is a boxplot depicting qualitative scores for mice in shredding nest material for control mice and in the tau mouse model rTg4510 expressing human mutant tau P301L, with efficient shredding scored at 3.5 or higher. Control litter-mates where able to shred their nest material efficiently while rTg4510 mice lost their ability in an age-related matter (score less than 1). Prolonged oral administration of 80 mg/Kg/day Lonafarnib in the absence (L80) or presence of Doxycicline (L80D) prevented the nest shredding deficit.

Example 2. Attenuation of the Behavioral Abnormalities in rTg4510 Mice by a Farnesyl Transferase Inhibitor As transgenic mice age, they display progressive worsening that begins with impaired marble burial and nest shredding and by 30 weeks progresses to hyperexcitability, restlessness in response to human approach and obsessive circling. Chronic intermittent (5 days on, 5 days off) lonafarnib treatment was applied protocol beginning at ten weeks of age. Nest building was assessed at 20 weeks. Wild-type littermates produced well-rounded nests; however untreated transgenic mice displayed poor nest shredding, and in some instances left bedding material completely untouched (FIG. 2). Lonafarnib treatment rescued nest building. At five weeks, littermate controls and transgenic mice produced nests with similar scores. While control mice nesting scores did not significantly change with time, transgenic mice scores declined.

Example 3. Farnesyl Transferase Inhibition with Lonafarnib Enhanced Lysosomal Protein Degradation To determine the mechanism of action of lonafarnib its previously suggested role in autophagy was explored. Using NIH3T3 mouse fibroblasts expressing the tandem reporter mCherry-GFP-LC3B[28] to monitor macroautophagy, lonafarnib treatment resulted in a dose-dependent increase in macroautophagy flux, as revealed by an overall increase in autophagic vacuoles mostly due to an increase in autolysosome abundance. At lower concentrations, the number of autophagosomes remained unchanged, suggesting their accelerated clearance by lysosomes. Similar results were reproduced in neuroblastoma N2a cells. The stimulatory effect of lonafarnib acted preferentially on basal macroautophagy as inferred by the fact that addition of lonafarnib to cells in which macroautophagy was induced either by paraquat or thapsigargin did not further increase macroautophagy flux.

The overall effect in all types of autophagy, but not the proteasome, suggested a direct effect of lonafarnib in endo/lysosomal compartments shared by all these autophagic pathways. To assess this possibility, proteolysis of long-half-life proteins was evaluated after a long pulse (48 h) with $^3$H-leucine. Indeed, lonafarnib increased proteolysis in a dose dependent manner, an effect that was abolished in the presence of NH$_4$Cl and leupeptin. These results support that lonafarnib treatment results in an overall improvement of lysosomal function and the pathways that mediate delivery of cargo to this compartment.

Example 4. Rhes Inhibition can Reduce Tau-Related Pathology

To demonstrate that the effect of lonafarnib on tau pathology in rTg4510 mice could in part be accounted for by the inhibition of Rhes farnesylation, Rhes levels were modulated directly. AAV vectors (overexpression or silencing) were injected into the right amygdala of 10 week-old rTg4510 mice. When analyzed at 20 weeks, Rhes silencing markedly reduced the number of MC1$^+$ neurons, reduced microgliosis, and increased the coronal section area. Therefore, Rhes inhibition recapitulated the effects of lonafarnib. Rhes over-expression did not appear to worsen the pathology.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of treating a tauopathy in a subject, comprising
    administering to the subject a pharmaceutical composition comprising a farnesyltransferase inhibitor;
    wherein the tauopathy is selected from the group consisting of corticobasal degeneration, argyrophilic grain disease, chronic traumatic encephalopathy, Niemann-Pick-C, Guam-AL S-Parkinson's-dementia, post-encephalitic Parkinson's disease, Subacute sclerosing panencephalitis, and progressive supranuclear palsy.

2. The method of claim 1, wherein
    the farnesyltransferase inhibitor is selected from the group consisting of: lonafarnib, tipifarnib, gingerol, gliotoxin, α-hydroxy farnesyl phosphonic acid, manumycin A, chaetomellic acid A, clavaric acid, FPT Inhibitor I, FPT Inhibitor II, FPT Inhibitor III, FTase Inhibitor I, FTase Inhibitor II, FTI-276 trifluoroacetate salt, GGTI-297, FTI-277 trifluoroacetate salt, and L-744,832 dihydrochloride.

* * * * *